US00PP33603P2

(12) United States Plant Patent
Schara

(10) Patent No.: US PP33,603 P2
(45) Date of Patent: Nov. 2, 2021

(54) ***SEMPERVIVUM* PLANT NAMED 'FIRE QUARTZ'**

(50) Latin Name: *Sempervivum hybrida*
Varietal Denomination: Fire Quartz

(71) Applicant: Volkmar Schara, Herrieden (DE)

(72) Inventor: Volkmar Schara, Herrieden (DE)

( * ) Notice: Subject to any disclaimer, the term of this patent is extended or adjusted under 35 U.S.C. 154(b) by 0 days.

(21) Appl. No.: 16/939,620

(22) Filed: Jul. 27, 2020

(51) Int. Cl.
*A01H 5/02* (2018.01)
*A01H 6/32* (2018.01)

(52) U.S. Cl.
USPC ..... Plt./263.1
CPC ..... *A01H 6/32* (2018.05)

(58) Field of Classification Search
USPC ..... Plt./263.1
CPC ..... A01H 5/02; A01H 5/12
See application file for complete search history.

(56) References Cited

PUBLICATIONS https://sempervivumgarten.de/sempervivum-rose-quartz.htm; Dec. 15, 2020; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new and distinct variety of *Sempervivum* named 'Fire Quartz' that is characterized by a fast-growing single rosette of thick succulent leaves arranged in whorls with reduced production of offsets and flowers and whose foliage color is conditioned by regional growing conditions and nursery practices. Foliage color ranges from bright orange-red and green when plants have been overwintered in cold conditions to purple-red and green when plants have not receiving any winter chilling.

1 Drawing Sheet

Genus and species: *Sempervivum hybrida.*
Variety denomination: 'Fire Quartz'.

BACKGROUND OF THE NEW PLANT

The present invention relates to a new variety of *Sempervivum* commonly known as Stonecrop, or Hens and Chicks, or Houseleek. The present invention is known botanically as *Sempervivum hybrida* and will be referred to hereinafter by the cultivar name 'Fire Quartz'.

*Sempervivums* are hardy perennial succulent plants which are grown and appreciated for the diversity of color and form in their foliage and for their tolerance of arid conditions. Many cultivars of *Sempervivum* are in commerce and involve a wide range of species and natural hybrids. *Sempervivums* are versatile in use and are grown in dry soils, rock gardens, and in containers. The genus *Sempervivum* is a member of the family Crassulaceae.

The inventor maintains in his nursery in Herrieden, Ansbach, Germany a large collection of *Sempervivums* including named varieties and unnamed and unreleased seedlings raised by the inventor. The inventor established his *Sempervivum* breeding programme in 1996 with the primary aim of developing a series of colorful varieties which form uniform large fast-growing rosettes with minimal production of offsets and flowers.

The inventor selected 'Fire Quartz' in 2014 as a seedling which the inventor had raised from seed resulting from the open pollination of *Sempervivum* 'Zundflamme' (unpatented), as female female parent. The identity of the male parent is unknown. 'Fire Quartz' was first asexually propagated in 2014 by the inventor at the inventor's nursery by removal of lateral offsets (known also as chicks or pups) and rooting the offsets in well-drained soil. Since that time, under careful observation, the distinguishing characteristics of 'Fire Quartz' have been determined stable and uniform and reproduced true to type in successive generations of asexual propagation.

SUMMARY

The following traits have been repeatedly observed and represent the distinguishing characteristics of the new *Sempervivum* variety named 'Fire Quartz'. These traits in combination distinguish 'Fire Quartz' from all other existing varieties of *Sempervivum* known to the inventor. 'Fire Quartz' has not been tested under all possible conditions. Phenotypic differences may be observed with variations in environmental, climatic, and cultural conditions.

1. Plants of 'Fire Quartz' exhibit a fast-growing single rosette of thick succulent leaves arranged in whorls.
2. The colors of the leaves of 'Fire Quartz' are conditioned by regional growing conditions and nursery practices.
3. When 'Fire Quartz' is grown from plants which have over-wintered in cold conditions, the spring and early summer foliage is bright orange-red and green in color.
4. When 'Fire Quartz' is grown from plants which have received winter greenhouse protection or have been grown in mild winter climates, the spring and early summer foliage is red-purple and green in color.
5. The new foliage growth which emerges in the center of the rosette is green in color.
6. Flowers of 'Fire Quartz' are rarely observed and only on plants which are at least two years old.

7. After one year of growth, plants of 'Fire Quartz' are 7 cm in height and 14 cm in diameter.
8. After two years of growth, plants of 'Fire Quartz' are 14 cm in height and 22 cm in diameter.
9. 'Fire Quartz' is hardy to USDA Zone 4.

COMPARISON WITH PARENTAL LINES AND KNOWN VARIETY

The inventor selected 'Fire Quartz' for its rapid production of very large rosettes compared to the many varieties in commerce. Whereas the female parent 'Zundflamme' produces a rosette of red or red-purple colored foliage, plants of 'Fire Quartz' grow more rapidly and achieve a greater size of plant in the same growing period. Typically, plants of 'Fire Quartz' are at least twice the size of same-aged plants of 'Zundflamme'.

Varieties of *Sempervivum* which resemble 'Fire Quartz' in their color combinations include *Sempervivum* 'Orion', *Sempervivum* 'Mystic' and *Sempervivum* 'Bedivere' (all unpatented). However, none of these varieties possesses the vigor and growth rate of 'Fire Quartz' which achieves at least twice the size as same-aged plants of these comparison varieties.

BRIEF DESCRIPTION OF THE PHOTOGRAPH

The accompanying photograph, FIG. 1, illustrates a two-year-old plant of 'Fire Quartz' which has been grown in a 2-gallon container out of doors in Oxnard, Calif. The photograph was taken in mid-July. The plant in the photograph has not received any winter chilling.

BOTANICAL DESCRIPTION OF THE PLANT

The following is a detailed botanical description of the new *Sempervivum* variety named 'Fire Quartz'. Observations, measurements, values and comparisons were collected in Oxnard, Calif. in July 2020 from a two-year-old plant which has been grown out of doors in a 2-gallon container without any winter chilling. Color determinations are made in accordance with The 2007 Royal Horticultural Society Colour Chart from London, England, except where general color terms of ordinary dictionary significance are used. The growing requirements of the new variety 'Fire Quartz' are similar to the species.

Botanical classification:
- *Family.*—Crassulaceae.
- *Genus and species.*—*Sempervivum hybrida.*
- *Denomination.*—'Fire Quartz'.
- *Common names.*—Stonecrop, Hens and Chicks, Houseleek.

Parentage:
- *Female Parent.*—*Sempervivum* 'Zundflamme'.
- *Male Parent.*—Unknown.

Plant:
- *Habit.*—Basal rosette.
- *Use.*—Garden and landscape planting, especially in dry conditions, planted containers.
- *Suggested commercial container size.*—4-inch container (1-year-old plants), 2-gallon container (2-year-old plants).
- *Propagation method.*—Removal and rooting of offsets.
- *Rooting system.*—Fine and fibrous.
- *Root color.*—NN155C.
- *Vigor.*—Fast-growing through spring and early summer.
- *Crop time.*—A 4-inch container will be filled out after four months from planting a rooted offset. A two-gallon container will be filled out after two years from planting a rooted offset.
- *Plant dimensions* (*two-year-old plant, 2-gallon container*).—14 cm in height and 22 cm in diameter.
- *Cultural requirements.*—Grown in free-draining soil and water sparingly in morning or evening.
- *Pest and disease resistance.*—None known to the inventor.
- *Pest and disease susceptibility.*—None known to the inventor.
- *Hardiness.*—USDA Zone 4.

Stem: Stemless.

Foliage:
- *Arrangement.*—Leaves arranged in whorls.
- *Whorl quantity* (*range*).—10-12.
- *Leaf quantity per whorl* (*range*).—20-25.
- *Leaf attachment.*—Sessile.
- *Leaf texture.*—Succulent, fleshy.
- *Leaf division.*—Simple.
- *Leaf margin.*—Finely ciliate, hairs evenly spaced 0.25-0.5 mm apart, length 0.25-0.5 mm, angled towards base, color NN155D.
- *Leaf surface:* (*abaxial and adaxial*).—Glabrous, semi-glossy.
- *Leaf shape.*—Obovate.
- *Leaf length* (*largest leaves*).—8 cm.
- *Leaf width* (*largest leaves*).—3 cm.
- *Leaf thickness* (*largest leaves*).—6 mm.
- *Leaf color.*—
- *Young leaves within tight rosette, unexposed to sunlight, both surfaces.*—144D-145A.
- *Older leaves in lower whorls, both surfaces.*—Transition with age from 144D-145A to predominantly 59A. Margins and apex remain 144D-145A until leaf fully expanded.
- *Leaf apex.*—Mucronate, spine 2-3 mm in length, soft, color 183A.
- *Leaf base.*—Truncate.
- *Venation.*—Absent.

Offsets:
- *Offset description.*—Emerge as whole plant rosettes on short stems within the older whorls. Stems lengthen with age. Offsets may be removed with stems attached for propagation.
- *Offset quantity.*—2-5 (2 only on observed plant).
- *Offset stem dimensions* (*if not removed*).—Up to 10 cm in length, 4 mm in diameter.
- *Offset dimensions.*—1.5-2.0 cm in height and diameter.
- *Offset foliage description.*—Whorled, leaves initially colored 144D-145A (both surfaces), becoming 59A on surfaces exposed to sunlight.

Inflorescence:
- *Inflorescences rarely observed and typical of the genus.*
- *Inflorescence type.*—Terminal cyme.
- *Inflorescence dimensions.*—6 cm. in height, 5 cm in diameter.
- *Blooming season.*—Late summer or fall.
- *Inflorescence quantity* (*if present*).—1 or 2.
- *Inflorescence stems* (*peduncles*).—Initially upright, emerging from within the rosette of whorls, not from the base. Stems arch as inflorescence ages and dies.

*Stem texture.*—Fleshy, surface downy.
*Stem dimensions.*—20-30 cm. in length, 3-5 mm in diameter.
*Stem color.*—144D-145A.
*Flower quantity.*—Approximately 50 per cyme.
*Flower shape.*—Stellar, radially symmetrical.
*Flower dimensions.*—5 mm in height, 6 mm in diameter.
*Fragrance.*—None observed.
*Lastingness of individual flower* (*on the plant*).—10-14 days.
*Persistent or self-cleaning.*—Persistent.

Bud:
*Bud shape.*—Spherical.
*Bud dimensions* (*immediately prior to opening*).—3-4 mm in diameter.
*Bud surface.*—Pubescent.
*Bud apex.*—Rounded.
*Bud color.*—26B.

Petals:
*Petal quantity.*—16.
*Petal color* (*both surfaces*).—36D, becoming NN155C when flower is fully expanded.
*Petal shape.*—Lanceolate.
*Petal apex.*—Acute.
*Petal base.*—Truncate.
*Petal margin.*—Smooth, entire.
*Petal dimensions.*—5 mm, 1 mm in width.
*Petal surface texture.*—Matte, paper-like.

Sepals:
*Sepal quantity.*—16.
*Sepal shape.*—Lanceolate.
*Sepal color.*—Ranges between 34A and 34C except 46A towards apex.
*Sepal apex.*—Acute.
*Sepal base.*—Truncate.
*Sepal margin.*—Smooth, entire.
*Sepal dimensions.*—3-4 mm in length, 1 mm in width.
*Sepal surface texture.*—Matte, abaxial surface pubescent.

Pedicel:
*Pedicel shape.*—Cylindrical.
*Pedicel color.*—34C.
*Pedicel surface texture.*—Glabrous.
*Pedicel dimensions.*—8 mm in length and 2 mm in width.

Reproductive organs:
*Stamens.*—24-32 in number, arranged in one or two concentric rings around central pistil cluster.
*Filaments.*—3-4 mm in length, color 46B.
*Anthers.*—Develop within orange-red membrane, color 45C.
*Pollen.*—Appears as membrane is shed, color 9A and bright, quantity moderate.
*Pistils.*—Approximately 12 in number.
*Style.*—Approximately 3 mm in length, color 17C.
*Stigma.*—Conical, color 34C.
*Ovary.*—Not observed.

Seed: Extremely fine, dust-like, color dark grey.

I claim:

1. A new and distinct cultivar of *Sempervivum* Plant Named 'Fire Quartz' as described and illustrated herein.

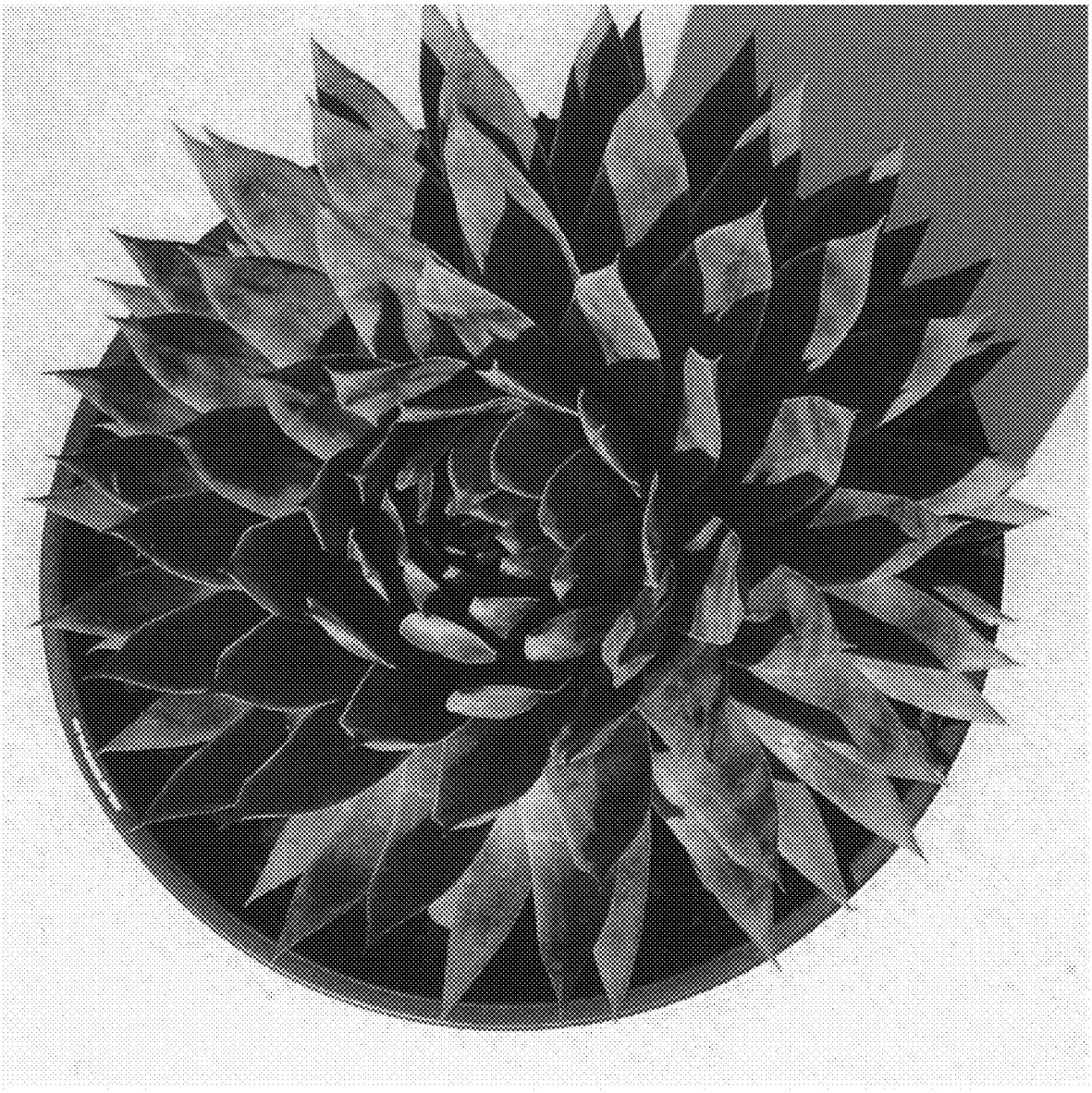

* * * * *